(12) United States Patent
Durairaj et al.

(10) Patent No.: US 7,276,571 B2
(45) Date of Patent: Oct. 2, 2007

(54) PROCESS FOR MAKING PHENYLENE DIOXYDIACETIC ACID AND USE THEREOF

(76) Inventors: Raj B. Durairaj, 123 Edgemeade Dr., Monroeville, PA (US) 15146; Michael N. Tackie, 4969 Ludwig Rd., Murrysville, PA (US) 15668

( * ) Notice: Subject to any disclaimer, the term of this patent is extended or adjusted under 35 U.S.C. 154(b) by 71 days.

(21) Appl. No.: 11/170,389

(22) Filed: Jun. 29, 2005

(65) Prior Publication Data

US 2007/0004898 A1    Jan. 4, 2007

(51) Int. Cl.
*C08G 64/00* (2006.01)

(52) U.S. Cl. ............... 528/194; 502/162; 502/167; 514/220; 514/253.01; 525/296; 528/195; 528/205; 528/271; 528/272

(58) Field of Classification Search ........... 514/220, 514/253.01; 528/194, 195, 206, 205, 271, 528/272; 502/162, 167; 525/296
See application file for complete search history.

(56) References Cited

U.S. PATENT DOCUMENTS

| | | | |
|---|---|---|---|
| 6,239,249 B1 * | 5/2001 | Keitoku et al. | 528/194 |
| 6,316,666 B1 * | 11/2001 | Morimoto et al. | 562/471 |
| 6,476,258 B1 | 11/2002 | Komatsu et al. | |
| 2001/0003775 A1 * | 6/2001 | Keitoku et al. | 528/271 |

FOREIGN PATENT DOCUMENTS

| | | | |
|---|---|---|---|
| EP | 1 026 146 A2 | | 8/2000 |
| EP | 1026146 | * | 8/2000 |
| JP | 04-091052 | | 3/1992 |
| JP | 04-173764 | | 6/1992 |

OTHER PUBLICATIONS

Written Opinion of the International Searching Authority, mailed Jan. 9, 2006.

* cited by examiner

*Primary Examiner*—Terressa Boykin

(57) ABSTRACT

A process for making phenylene dioxydiacetic acid comprises (a) contacting a dihydroxybenzene under reaction conditions with a salt of haloacetic acid in a solution without adding a haloacetic acid to produce a salt of phenylene dioxydiacetic acid; and (b) optionally converting the salt of phenylene dioxydiacetic acid to free phenylene dioxydiacetic acid. In some embodiments, 1,3-phenylene dioxydiacetic acid (RDOA) is made by reacting resorcinol with sodium chloroacetic acid in a reaction mixture with a pH in the range of about 7 to about 11 and at a temperature from about 70° C. to 105° C. By adjusting the reactions conditions, a relatively high yield of 1,3-phenylene dioxydiacetic acid (i.e., greater than 80%) is obtained. The purified acid can be used in the synthesis of polyester, such as polyethylene terephthalate.

38 Claims, No Drawings

PROCESS FOR MAKING PHENYLENE DIOXYDIACETIC ACID AND USE THEREOF

PRIOR RELATED APPLICATIONS

Not applicable.

FEDERALLY SPONSORED RESEARCH STATEMENT

Not applicable.

REFERENCE TO MICROFICHE APPENDIX

Not applicable.

FIELD OF THE INVENTION

The invention relates to methods of making phenylene dioxydiacetic acid and uses thereof.

BACKGROUND OF THE INVENTION

Polyester resins, represented by polyethylene terephthalate ("PET"), possess excellent mechanical properties and chemical properties, e.g., excellent transparency, gas barrier properties, safety and sanitation and the like. As such, they have been used widely particularly in the food packaging field, as bottles obtained by stretch blow molding of an injection-molded preform, as trays or cups obtained by thermoforming of an extrusion-molded sheet, or as films obtained by biaxial stretching of the sheet.

PET can be made by condensing ethylene glycol and terephthalic acid. To increase its gas barrier properties, resorcinol di(oxyacetic) acid (RDOA) or 1,3-phenylene dioxydiacetic acid has been used as a co-monomer in the polymerization process. The use of the RDOA monomer was found to be effective in enhancing the barrier properties of polyesters, polyamides and their copolymers.

RDOA can be synthesized from resorcinol from two different routes. In the first method, resorcinol is first converted into bis(hydroxyethyl)ether of resorcinol, which is subsequently oxidized to produce RDOA. In the second method, RDOA can be obtained directly from the reaction of resorcinol with chloroacetic acid under alkaline conditions. Of these two methods, the chloroacetic acid route could be more economical and straight forward, but the yield of RDOA obtained from the chloroacetic acid route has been often relatively low due to the formation of various by-products.

Therefore, there is a need for a process to make 1,3-phenylene dioxydiacetic acid (i.e., RDOA) and its analogs in a relatively higher yield. Preferably, the process also produces relatively higher purity products.

SUMMARY OF THE INVENTION

The aforementioned need is fulfilled by various aspects of the invention. In one aspect, the invention relates to a method of making a phenylene dioxydiacetic acid. The method comprises contacting a dihydroxybenzene under reaction conditions with a salt of haloacetic acid in a solution without adding a haloacetic acid to produce a salt of phenylene dioxydiacetic acid; and optionally converting the salt of phenylene dioxydiacetic acid to free phenylene dioxydiacetic acid.

In some embodiments, dihydroxybenzene is resorcinol, hydroquinone, or catechol. Preferably, dihydroxybenzene salt is not used as a starting material. In other embodiments, the salt of haloacetic acid is formed by reacting a hydroxide with a haloacetic acid before contacting the dihydroxybenzene. In some embodiments, the reaction mixture obtained in the contacting step has a pH value in the range from about 7 to about 11, from about 8 to about 10, or from about 8.5 to about 8.9. In other embodiments, the reaction mixture obtained in the contacting step is kept at a temperature in the range from about 70° C. to about 105° C., from about 80° C. to about 95° C., or about 85° C. In some embodiments, a stoichiometric amount of the salt of a haloacetic acid is contacted with the dihydroxybenzene. In other embodiments, a molar excess amount of the salt of a haloacetic acid is contacted with the dihydroxybenzene. Preferably, the salt of a haloacetic acid is added to the reaction mixture stepwise. The molar excess amount is about 20% to about 30%. The pH of the reaction mixture can be adjusted by adding an appropriate amount of an alkaline solution. The conversion of the salt of phenylene dioxydiacetic acid to free phenylene dioxydiacetic acid can be effected by contacting the salt with an acid, and the acid can be hydrochloric acid, sulfuric acid or mineral acid. In some embodiments, the salt of haloacetic acid is sodium monochloroacetate or sodium monobromoacetate. Preferably, the dihydroxybenzene is resorcinol and the salt of a haloacetic acid is sodium chloroacetate.

In another aspect, the invention relates to a method of making 1,3-phenylene dioxydiacetic acid which comprises contacting resorcinol with sodium chloroacetate in an aqueous solution without adding a chloroacetic acid at a temperature from about 70° C. to about 95° C. and a pH from about 8.5 to 8.9 to produce sodium 1,3-phenylene dioxydiacetate. The method further comprises converting the sodium 1,3-phenylene dioxydiacetate into free 1,3-phenylene dioxydiacetic acid. Preferably, the sodium chloroacetate is prepared by reacting a stoichiometric amount of sodium hydroxide with chloroacetic acid before contacting with the resorcinol.

In yet another aspect, the invention relates to a method of making copolymerized polyester resin which comprises subjecting a dicarboxylic acid component containing terephthalic acid or its ester derivative as the main component and a phenylene dioxydiacetic acid obtained from the method of claim 1 as a copolymerizable component, and a diol component containing ethylene glycol as the main component, to polycondensation through an esterification reaction or a transesterification reaction. Either batch or continuous processes can be used.

Additional aspects of the invention and advantages and characteristics provided by various embodiments of the invention become apparent with the following description.

DESCRIPTION OF EMBODIMENTS OF THE INVENTION

In the following description, all numbers disclosed herein are approximate values, regardless whether the word "about" or "approximate" is used in connection therewith. They may vary by 1 percent, 2 percent, 5 percent, or, sometimes, 10 to 20 percent. Whenever a numerical range with a lower limit, $R^L$ and an upper limit, $R^U$, is disclosed, any number falling within the range is specifically disclosed. In particular, the following numbers within the range are specifically disclosed: $R=R^L+k*(R^U-R^L)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed.

Embodiments of the invention provide a method of making a phenylene dioxydiacetic acid. The method comprises contacting a dihydroxybenzene under reaction conditions with a salt of haloacetic acid in a solution without adding a haloacetic acid to produce a salt of phenylene dioxydiacetic acid; and optionally converting the salt of phenylene dioxydiacetic acid to free phenylene dioxydiacetic acid. Preferably, the salt of haloacetic acid is soluble in the solution, and the solution is water or alcohol. By adjusting the reaction conditions, phenylene dioxydiacetic acids are obtained in a relatively high yield. In some embodiments, high purity phenylene dioxydiacetic acids are obtained. The term "yield" is defined as the percentage of the actual amount of the acid obtained relative to the theoretical amount. Generally, the phenylene dioxydiacetic acid yield is at least about 70%. In some embodiments, the yield is greater than about 75%. In other embodiments, the yield is greater than about 80%. Under certain reactions conditions, it is greater than about 85% or even greater than about 90%.

Suitable dihydroxybenzenes are represented by formula (1) below:

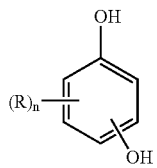

(1)

wherein R represents a hydroxyl, halogen, carboxyl group or hydrocarbon group, and n represents an integer from 0 to 3. Preferably, the hydrocarbon group has one to four carbon atoms per group. Examples of the dihydroxybenzenes of formula (1) include, but are not limited to, resorcinol, hydroquinone, and catechol. Recorcinols can be unsubstituted or substituted. Examples of substituted resorcinols includes, but are not limited to, 5-methylresorcinol, 5-ethylresorcinol, 5-propylresorcinol, 2-methylresorcinol, 4-methylresorcinol, 4-ethylresorcinol, 4-propylresorcinol, 2-ethylresorcinol, 2-propylresorcinol, and 2-butylresorcinol. Suitable salts include any monovalent metal salts. Preferably, the salts are soluble in the water or alcohol. An example of monovalent metals is alkali metals, such as Li, Na, K, Rb, and Cs.

The phenylene dioxydiacetic acids obtained from the above process are represented by formula (2), where R and n are defined above.

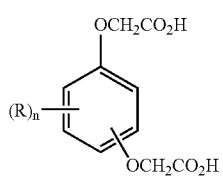

(2)

Specific examples of the acids include, but are not limited to, 1,2-phenylene dioxydiacetic acid, 1,3-phenylene dioxydiacetic acid, 1,4-phenylene dioxydiacetic acid, 2-methyl-1,3-phenylene dioxydiacetic acid, 5-methyl-1,3-phenylene dioxydiacetic acid, 6-methyl-1,3-phenylene dioxydiacetic acid, 5-ethyl-1,3-phenylene dioxydiacetic acid, 6-ethyl-1,3-phenylene dioxydiacetic acid, 5-methoxy-1,3-phenylene dioxydiacetic acid, 6-methoxy-1,3-phenylene dioxydiacetic acid, 4-methyl-1,3-phenylene dioxydiacetic acid, 4-ethyl-1,3-phenylene dioxydiacetic acid, 4-propyl-1,3-phenylene dioxydiacetic acid, 2-ethyl-1,3-phenylene dioxydiacetic acid, 4-chloro-1,2-phenylene dioxydiacetic acid, 4-chloro-1,3-phenylene dioxydiacetic acid, 2-chloro-1,4-phenylene dioxydiacetic acid, 2-methyl-1,4-phenylene dioxydiacetic acid, and 2-ethyl-1,4-phenylene dioxydiacetic acid.

Suitable salts of haloacetic acid include any salt that is water soluble and capable of reacting with dihydroxybenzene to form the salt of phenylene dioxydiacetic acid. The salts of haloacetic acid can be represented by formula (3)

$$XCH_2COOM \quad (3)$$

wherein X is a halogen, such as fluorine, chlorine, bromine, and iodine. Preferably, X is either chlorine or bromine. M is a monovalent metal, such as a Group IA metal. Preferably, it is Li, Na, K, or Rb. Such salts can prepared by the following reaction:

$$XCH_2COOH + MOH \rightarrow XCH_2COOM + H_2O$$

In some embodiments of the invention, no external haloacetic acid, such as chloroacetic acid, is added to the reaction mixture because its salt is used instead. While dihydroxybenzene, not its salt, is used in some embodiments, a salt of dihydroxybenzene can be used in place of dihydroxybenzene partially or totally in other embodiments. In some embodiments, the pH of the reaction mixture is in the range from about 7 to about 11, preferably from about 8 to about 10 or 8.5 to about 9. In other embodiments, the temperature of the reaction mixture is in the range of from about 70° C. to about 105° C., preferably from about 85° C. to about 95° C. or about 85° C.

1,3-phenylene dioxydiacetic acid can be prepared according to the following reaction scheme. In the following reactions, resorcinol reacts with sodium hydroxide to form sodium resorcinate in situ. Then the in-situ generated sodium resorcinate reacts with the salt of chloroacetic acid to form the salt of 1,3-phenylene dioxydiacetic acid. The free acid can be obtained by contacting the salt with an acid, such as sulfuric acid. As discussed above, the in situ generated sodium resorcinate may be replaced by providing external sodium resorcinate to the reaction mixture, preferably in a low concentration which is continuously replenished as it reacts with the salt of chloroacetic acid. "Low concentration" means that sodium recorcinate is less than about 50% of the stoichoimetric amount need to react with the salt of chloroacetic acid to form the salt of 1,3-phenylene dioxydiacetic acid. In some embodiments, it is less than about 20%, less than about 10%, or less than about 5%. In other embodiments, it is less than about 2% or less than about 1%.

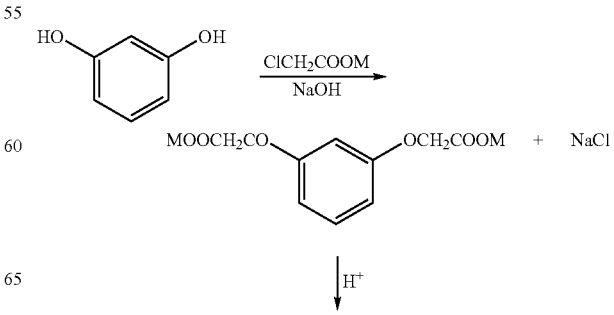

-continued

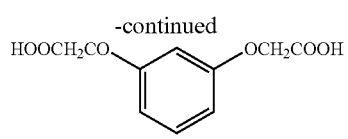

In accordance with the above reaction scheme, 1,3-phenylene dioxydiacetic acid can be prepared in two steps: (1) formation of sodium chloroacetate; and (2) reaction of sodium chloroacetate with resorcinol or a salt thereof. In the first step of the process, chloroacetic acid is charged to a vessel, and mixed with water to obtain an aqueous solution. This solution is chilled to a temperature below room temperature but above 0° C. This temperature is preferably between about 5° C. and about 30° C., preferably between 10° C. and 20° C. To the chilled chloroacetic acid solution, an aqueous sodium hydroxide solution is added dropwise over an hour. The NaOH is added in the precise amount to form sodium chloroacetate. The sodium chloroacetate solution is maintained in the chilled state until it is needed.

In the second step of the process, resorcinol is charged to a reaction vessel. Water is added to make an aqueous solution, and a portion of the sodium chloroacetate solution prepared in the first step is added to the vessel. The amount of sodium chloroacetate added to the reaction vessel can be varied. It has been found that initially adding a stoichiometric amount is beneficial. In other words, for every mole of resorcinol, two mole equivalents of sodium chloroacetate are added. The vessel and its contents are then heated to the reaction temperature. It is preferred to carry out this reaction at temperatures between 70 and 105° C., which is roughly where the contents will reflux. More preferably, the temperature should be between 70 and 95° C., and most preferably, it should be about 85° C. Once the reaction temperature is reached, aqueous sodium hydroxide solution is added in such a way that the pH is maintained at a target point. This reaction has been carried out successfully in pH ranges of from 7.2 to 11, but it has been found advantageous to use a pH of in the range of about 8.5 to about 8.9.

It has been found that pH control is important. Any suitable high-quality pH probe may be used, but it has been found that the Orion Ross pH probes from Orion Research Corporation are particularly suitable. As the reaction progresses, the solubility limit of RDOA in water is exceeded. When this happens, the RDOA will begin to plate out onto the pH probe, making readings erroneous. For this reason, a probe which is fast-responding and which can be flushed during use is preferred.

It also has been found that when either the pH or temperature is too high, a by-product as represented by formula (4) forms, which is a rearrangement product of RDOA.

(4)

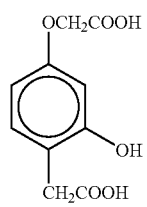

It is technically referred to as 3-hydroxy-4-(carboxymethyl)phenoxyacetic acid ("HCPA"). This is another reason why the reaction conditions should be carefully controlled. For this reason, the temperature should be kept at 105° C. or less, even though the reaction is accelerated at higher temperatures. Moreover, the pH should be kept less than 11, preferably less than 10.

During NaOH addition, once the pH has stabilized, a second portion of the sodium chloroacetate is added. As stated previously, the sodium chloroacetate can be added in any proportions, but it has been found preferable to perform the addition in three stages, corresponding to 1:0.15:0.15 in mole ratios. It has been found that a molar excess of about 20-30% of chloroacetic acid gives optimum yields. After the addition of the second portion of sodium chloroacetate, the NaOH solution is again dripped in as needed to control the pH. When the pH stabilizes without further addition of NaOH, the final portion of sodium chloroacetate is added. When the pH is controlled and stabilized for the final time, a mineral acid is then added to precipitate the RDOA formed. The use of mineral acid to purify RDOA is disclosed in U.S. Pat. No. 6,316,666, which is incorporated by reference herein in its entirety.

In some embodiments, sulfuric acid and hydrochloric acid are used to reduce pH for precipitation. Of the two, hydrochloric acid is preferred because it produces sodium chloride, the same salt that is produced during the synthesis. The problem of disposing of a mixture of two salts is thereby avoided.

The RDOA product can be recovered by filtration and washing to obtain the purified material. If desired, recrystallization as practiced in the art may also be employed. The RDOA can be classified into two purity specifications: crude and high purity. The difference between the two is that the crude is not recrystallized, whereas the high purity material has been recrystallized in ethyl alcohol or other organic solvent.

Typically, crude RDOA may contain up to 1.5 wt. % each of resorcinol mono(oxyacetic) acid ("RMOA") and HCPA. Recrystallization reduces the HCPA content by about 60%, and the RMOA by 75%. About 2-4% of the ethyl ester of RDOA is found in the recrystallized material where ethanol was used as a crystallization solvent. It has been found that recrystallization solvents such as ethanol, ethanol/water, methanol, methanol/water, toluene, xylene are suitable for recrystallization. This is not an exhaustive list; in addition, any of the lower alcohols are suitable for recrystallization and may be used for this purpose. The melting point of the material obtained is 192-194° C., with a purity of 98.5% for crude, or 99.8% when recrystallized.

Purified phenylene dioxydiacetic acids, such as 1,3-phenylene dioxydiacetic acid, prepared in the above processes can be used in the synthesis of polyester. Numerous methods exist for polyester synthesis. Such methods are disclosed, for example, in U.S. Pat. No. 6,239,249, which is incorporated by reference herein in its entirety. Specifically, polyester resins can be prepared from polycondensation of a dicarboxylic acid component containing terephthalic acid or its ester derivative as the main component and a diol component containing ethylene glycol as the main component. Namely, it may be any of a direct polymerization method wherein the dicarboxylic acid component containing terephthalic acid as the main component and the diol component containing ethylene glycol as the main component are subjected to esterification in an esterification reaction tank, and the obtained esterification reaction product is transferred to a polycondensation reaction tank for polycondensation; a transesterification method wherein the dicarboxylic acid component containing an ester derivative of terephthalic acid as the main component and the diol component containing ethylene glycol as the main component are subjected to transesterification reaction in a transesterification reaction tank, and the obtained transesterification reaction product is transferred to a polycondensation reaction tank for polycondensation; or a continuous direct polymerization method wherein a slurry obtained by dispersing the dicarboxylic acid component containing terephthalic acid as the main component, into the diol component containing ethylene glycol as the main component, in a slurry preparation tank, is continuously added to the esterification reaction product or the transesterification reaction product in the esterification reaction tank obtained as mentioned above, for esterification under normal pressure, and the obtained reaction product is transferred to the polycondensation reaction tank continuously and/or by stages, for polycondensation. Further, the resin obtained by the polycondensation reaction is usually drawn in a form of a strand from a drawing aperture provided at the bottom of the polycondensation reaction tank, and is cut by a cutter during or after cooling with water, to have a form of pellets. When the pellets after the polycondensation are subjected to heat treatment for solid state polymerization, a higher degree of polymerization can be obtained, and besides, formation of e.g. acetaldehyde and a low molecular weight oligomer as by-products can be decreased.

In the above-mentioned production method, the esterification reaction is carried out at a temperature of from about 200° C. to about 270° C. under a pressure of from 0 to about 3 kg/cm² G in the presence of a catalyst for esterification, e.g., an organic acid salt such as diantimony trioxide, antimony, titanium, magnesium or calcium as the case requires. The polycondensation reaction is carried out at a temperature from about 240 to about 290° C. under a reduced pressure from about 0.1 to about 10 mmHg in the presence of a catalyst for polycondensation, e.g., a metal oxide such as germanium dioxide, germanium tetraoxide or diantimony trioxide, or an organic acid salt such as germanium, antimony, zinc, titanium or cobalt, and a stabilizer such as phosphoric acid, phosphorous acid or an alkyl phosphate. Further, the solid state polymerization is carried out at a temperature from about 180 to about 240° C. in an atmosphere of an inert gas such as nitrogen gas and/or under a reduced pressure from about 0.1 to about 10 mmHg, after preliminary crystallization is carried out by heating at a temperature from about 120 to about 200° C. for at least 1 minute.

In the method for producing a polyester resin, it is preferable to add the phenylene dioxydiacetic acid as the copolymerizable component in the dicarboxylic acid component to the reaction system in the form of a solution dissolved in the diol component. The copolymerization can be carried out stably, and accordingly, production of polyester resins having a stable quality is made possible.

Here, the diol component to be used for dissolution is not particularly limited so long as it is ethylene glycol or another diol component to be used for copolymerization. Preferred is ethylene glycol, and the molar ratio of the diol component for dissolution in the solution to the phenylene dioxydiacetic acid is preferably from 2 to 12, more preferably from 2.5 to 8, particularly preferably from 3.5 to 5, in view of solubility and fluidity of the solution. The dissolution is carried out at a temperature of preferably a level of from 50 to 180° C.

With respect to the addition of the above-mentioned phenylene dioxydiacetic acid solution to the reaction system, a method of adding the solution to the esterification reaction tank at the initiation of, or during, the esterification reaction or the transesterification reaction, or a method of adding the solution to the esterification reaction product or the transesterification reaction product in the esterification reaction tank, in a transfer pipe through which the product is transferred from the esterification reaction tank to the polycondensation reaction tank, or in the polycondensation reaction tank to which the product is transferred, may, for example, be mentioned. Among these, it is preferred to add the solution to the esterification reaction product or the transesterification reaction product. The solution is added to the reaction system at a temperature of preferably from 30 to 150° C., more preferably from 50 to 100° C.

Particularly preferably, the solution having the phenylene dioxydiacetic acid dissolved in the diol component, is added to the reaction system in the presence of the esterification or transesterification reaction product obtained at any time after the initiation of the esterification or transesterification reaction of the dicarboxylic acid component except for the phenylene dioxydiacetic acid and the diol component, and before the initiation of the polycondensation reaction, after addition of a phosphorus compound as the stabilizer before addition of the catalyst for polycondensation, whereby the formation of the foreign substances can be decreased.

The above-mentioned addition of the solution in the presence of the esterification or transesterification reaction product obtained at any time after the initiation of the esterification or transesterification reaction before the initiation of the polycondensation reaction, specifically represents addition of the solution to the esterification or transesterification reaction product immediately after the initiation of the esterification or transesterification reaction, during the esterification or transesterification reaction, or after the completion of the esterification or transesterification reaction, in the esterification reaction tank, in the transfer pipe from the esterification reaction tank to the polycondensation reaction tank, or in the polycondensation reaction tank. Among these, it is more preferred to add the solution to the esterification or transesterification reaction product after the completion of the esterification or transesterification reaction in the polycondensation reaction tank before the product is transferred.

In the case where the phenylene dioxydiacetic acid solution is added to the esterification reaction tank before or at the initiation of the esterification or transesterification reaction, or to the esterification reaction tank after the completion of the esterification or transesterification reaction before the transfer of the reaction product to the polycondensation reaction tank, the phenylene dioxydiacetic acid is likely to deteriorate by heat, and the obtained polyester resin tends to be poor in color tone.

With respect to the addition of the phenylene dioxydiacetic acid solution after the addition of the phosphorous compound and before the addition of the catalyst for polycondensation, specifically, the solution is added preferably at least 5 minutes, more preferably at least 10 minutes, after the addition of the phosphorous compound, and the catalyst for polycondensation is added preferably at least 5 minutes, more preferably at least 10 minutes, after the addition of the solution. It is preferred to add the phosphorous compound and the catalyst for polycondensation in the form of solutions dissolved in the above-mentioned diol component, preferably in ethylene glycol, respectively.

The phosphorous compound to be used may, for example, be phosphoric acid, phosphorous acid, hypophosphorous acid or polyphoshoric acid, or an ester thereof, or a phosphine or a phosphite. The amount is preferably from 20 to 400 ppm, particularly preferably from 40 to 340 ppm, as the phosphorous compound based on the theoretical yield of the polyester resin.

The catalyst for polycondensation to be used is as defined above, and the amount is preferably from 10 to 400 ppm, particularly preferably from 30 to 300 ppm, as the compound to be used based on the theoretical yield of the polyester resin.

With respect to the polyester resin obtained by the production method, a preform obtained by injection molding is subjected to stretch blow molding, or a sheet obtained by extrusion molding is subjected to thermoforming to be molded into e.g. trays and containers, or the sheet is subjected to biaxial stretching to obtain e.g. films.

Particularly, the polyester resin is suitable for making bottles by blow molding such as cold parison method wherein biaxial stretching of the preform obtained by injection molding is carried out after reheating. The bottles are suitably used as containers for drinks such as carbonated drinks, fruit juice, alcohol drinks, tea and mineral water, and for liquid flavorings such as soy sauce, Worcestershire sauce, sweet sake and dressing.

The following examples are presented to exemplify embodiments of the invention. All numerical values are approximate. When numerical ranges are given, it should be understood that embodiments outside the stated ranges may still fall within the scope of the invention. Specific details described in each example should not be construed as necessary features of the invention.

Preparation of Sodium Chloroacetate: Into a round-bottomed flask equipped with a magnetic stirrer, thermometer and addition funnel, chloroacetic acid dissolved in water was placed. The NaOH solution was dripped into the stirred chloroacetic acid solution. The solution was chilled with ice/water in a container. Care was taken to keep the temperature of the solution below 30° C. Under these conditions, the hydrolysis of the chloroacetic acid to glycolic acid was suppressed. The sodium chloroacetate, when made in this way, is stable in a refrigerator for several days.

EXAMPLE 1

Into a 500 ml reaction kettle equipped with a mechanical stirrer, cold condenser, thermometer and an addition funnel, 16 grams of sodium hydroxide (NaOH, 0.4 mole) dissolved in 45 grams of water were added. Then 22 grams of resorcinol (0.2 mole) were added under nitrogen atmosphere and stirred well to form the disodium salt of resorcinol. After this, 38 grams of chloroacetic acid (0.4 mole) were added and mixed thoroughly. The reaction mixture was heated to about 50 to 55° C., and then an aqueous solution prepared from 16 grams of NaOH dissolved in 45 grams of distilled was added slowly over a period of 30 minutes at this temperature. After the addition, the reaction mixture was heated to reflux (95 to 100° C.) and held for 60 minutes at this reflux condition. Then the reaction mixture was cooled to about 80 to 85° C. The resulting product appeared as a slurry. Then, the dilute sulfuric acid, prepared from the solution of 36.8 grams of concentrated sulfuric acid (0.38 mole) with 20 grams of distilled water, was added slowly into the reaction slurry containing the sodium salt of resorcinol di(oxyacetic) acid at 80 to 85° C. The pH of the solution after the acidification step was in the range of about 0.5 to 1.0. During the acidification process, the crystals of resorcinol di(oxyacetic) acid started to separate out of the solution.

Thereafter, the acidified reaction mixture was cooled to room temperature. The precipitated crystals were filtered and washed with 160 grams of distilled water. Finally, the wet product was first dried under atmospheric conditions and then vacuum dried at about 50 to 70° C. to obtain the crude resorcinol di(oxyacetic) acid (RDOA). The above process is illustrated below as Process Scheme 1. In general, the yields based on this process vary between 55 to 65 weight percent. NMR analysis was performed to determine the purity of RDOA as well as the presence of other impurities, such as resorcinol mono(oxyacetic) acid (RMOA) and 3-hydroxy-4-carboxymethylphenoxyacetic acid (HCPA) present in the crude reaction mixture.

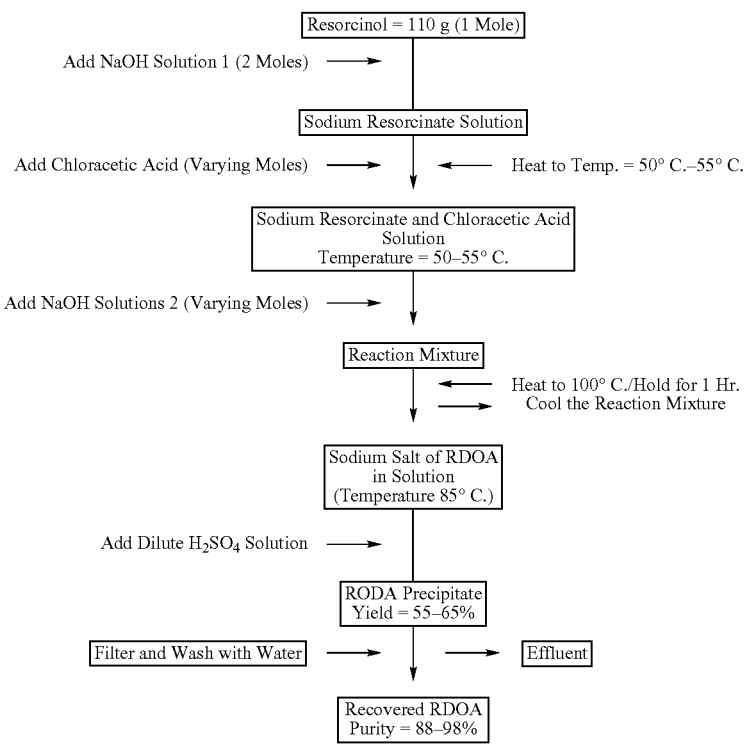

Process Scheme 1

EXAMPLES 2 THROUGH 4

The synthesis details of resorcinol di(oxyacetic) acid from the reaction of sodium resorcinate and varying molar ratios of chloroacetic acid are presented in Table 1 below. These examples are also based on the method illustrated as Process Scheme 1 above.

dried. The product yield, melting point and NMR analysis result of the RDOA material are given in Table 2.

EXAMPLES 8 THROUGH 10

Example 7 was repeated with increasing molar quantity of sodium chloroacetate and maintaining the reaction pH at 8.2. The results from these experiments are presented in Table 2.

TABLE 1

Synthesis of Resorcinol Di(Oxyacetic) Acid (RDOA)
(Sodium Resorcinate and Chloroacetic Acid in the Pot; Process Scheme 1)

|  | Example 1 | | Example 2 | | Example 3 | | Example 4 | |
| --- | --- | --- | --- | --- | --- | --- | --- | --- |
|  | Moles | Grams | Moles | Grams | Moles | Grams | Moles | Grams |
| Raw Materials | | | | | | | | |
| Resorcinol | 0.2 | 22 | 0.2 | 22 | 0.2 | 22 | 0.2 | 22 |
| NaOH Solution 1 (for Resorcinol) | 0.4 | 16 | 0.4 | 16 | 0.4 | 16 | 0.4 | 16 |
| Chloroacetic Acid | 0.4 | 38 | 0.44 | 41.6 | 0.5 | 47.5 | 0.54 | 51 |
| NaOH Solution 2 (for Reaction) | 0.4 | | 0.44 | | 0.5 | | 0.54 | |
| Dilute H2SO4 (for Neutralization) | 0.38 | | 0.38 | | 0.38 | | 0.38 | |
| Reacation Conditions | | | | | | | | |
| NaOH Addition Temperature (° C.) | 50-55 | | 50-55 | | 50-55 | | 50-55 | |
| NaOH Addition Time (Minutes) | 60 | | 155 | | 168 | | 168 | |
| Molar Excess of Chloroacetic Acid (%) | 0 | | 10 | | 25 | | 35 | |
| Acid Addition Temp. (° C.) | 80-85 | | 80-85 | | 80-85 | | 80-85 | |
| Product Yield (RDOA) | | | | | | | | |
| Expected Yield (Theoretical, g) | 45.2 | | 45.2 | | 45.2 | | 45.2 | |
| Actual Yield (g) | 27.6 | | 29.8 | | 27.2 | | 26.4 | |
| Actual Yield (%) | 61 | | 66 | | 60 | | 58 | |
| Melting Point (° C.) | 187-192 | | 187-193 | | 188-192 | | 188-192 | |
| NMR Analysis of Product (Wt. %) | | | | | | | | |
| RDOA | 98.2 | | 89 | | 91 | | 95 | |
| RMOA | 2.8 | | 3.2 | | 2.5 | | 3 | |

The RDOA yields obtained from the Process Scheme 1 were observed to be relatively lower, i.e., in the range of from about 58% to about 66%. Though the amount of chloroacetic acid used in the reaction was higher (35 mole % excess) than the stoichiometric quantity required per mole of resorcinol, the RDOA yields did not improve from this process.

EXAMPLE 7

Into a 500 ml round-bottomed flask equipped with a stirrer, condenser, thermometer, pH probe and addition funnel, 22 grams of resorcinol (0.2 mole) and 0.4 mole of sodium chloroacetate (prepared using 38 grams of chloroacetic acid, 16 grams of sodium hydroxide and 45 grams of water) solution were added. The mixture was heated to about 100° C. Then 0.4 mole of aqueous sodium hydroxide solution (prepared from 16 grams of sodium hydroxide and 45 grams of water) was slowly added into the resorcinol and sodium chloroacetate solution in such a way that the pH was maintained at 8.2 during the addition. The addition time for NaOH solution was about 75 to 80 minutes. After this, the reaction mixture was stirred for an additional period of 30 to 60 minutes at 95 to 100° C. Then the mixture was cooled to about 85 to 90° C., and 0.38 mole of dilute sulfuric acid solution was added dropwise to bring the pH to about 0.5 to 1.0. The solution was cooled to room temperature, and the crystals separated were filtered, washed with water and

TABLE 2

Synthesis of Resorcinol Di(Oxyacetic) Acid (RDOA) Using Sodium Chloroacetate
Effect of Varying Sodium Chloroacetate Amount on RDOA Yield at pH = 8.2

|  | Example 7 Moles | Example 8 Moles | Example 9 Moles | Example 10 Moles |
| --- | --- | --- | --- | --- |
| Raw Materials | | | | |
| Resorcinol | 0.2 | 0.2 | 0.5 | 0.5 |
| Sodium Chloroacetate | 0.4 | 0.45 | 1.2 | 1.3 |
| Sodium Hydroxide Solution | 0.4 | 0.4 | 1.2 | 1.2 |
| Dilute H2SO4 (for Neutralization) | 0.38 | 0.38 | 1.2 (HCl) | 1.2 (HCl) |
| Reacation Conditions | | | | |
| Temperature (° C.) | 100 | 102 | 95 | 95 |
| pH of Reaction Mixture | 8.2 | 8.2 | 8.2 | 8.2 |
| Molar Excess of Chloroacetate (%) | 0 | 12.5 | 20 | 30 |
| Chloroacetate Addition Steps (#) | 1 | 2 | 3 | 3 |
| Acid Addition Temp. (° C.) | 90-95 | 90-95 | 90-95 | 90-95 |

TABLE 2-continued

Synthesis of Resorcinol Di(Oxyacetic) Acid (RDOA) Using Sodium Chloroacetate

Effect of Varying Sodium Chloroacetate Amount on RDOA Yield at pH = 8.2

| | Example | | | |
|---|---|---|---|---|
| | 7 Moles | 8 Moles | 9 Moles | 10 Moles |
| Product Yield (RDOA) | | | | |
| Expected Yield (Theoretical, g) | 45.2 | 45.2 | 113.1 | 113.1 |
| Actual Yield (g) | 36.4 | 37.7 | 93.1 | 89.1 |
| Actual Yield (%) | 80 | 83 | 82 | 79 |
| Melting Point (° C.) | 184-200 | 187-191 | 182-190 | 182-189 |
| NMR Analysis of Product (Wt. %) | | | | |
| RDOA | 61 | 95.6 | 87 | 98 |
| RMOA | 13 | 2.6 | 11 | 1.1 |
| HCPA | 0.6 | 0 | 0.5 | 0.5 |

As can be seen from Table 2 results, the use of sodium chloroacetate in the place of chloroacetic acid appears to improve the resorcinol di(oxyacetic) acid yield.

EXAMPLE 11

In order to determine the effect of pH, and also with the use of 30% molar excess of sodium chloroacetate in the preparation, on the yield of RDOA, the following experiments were conducted. In these experiments, three step additions of sodium chloroacetate and sodium hydroxide solutions have been performed. These preparations were based on the following procedures which are illustrated as Process Scheme 2.

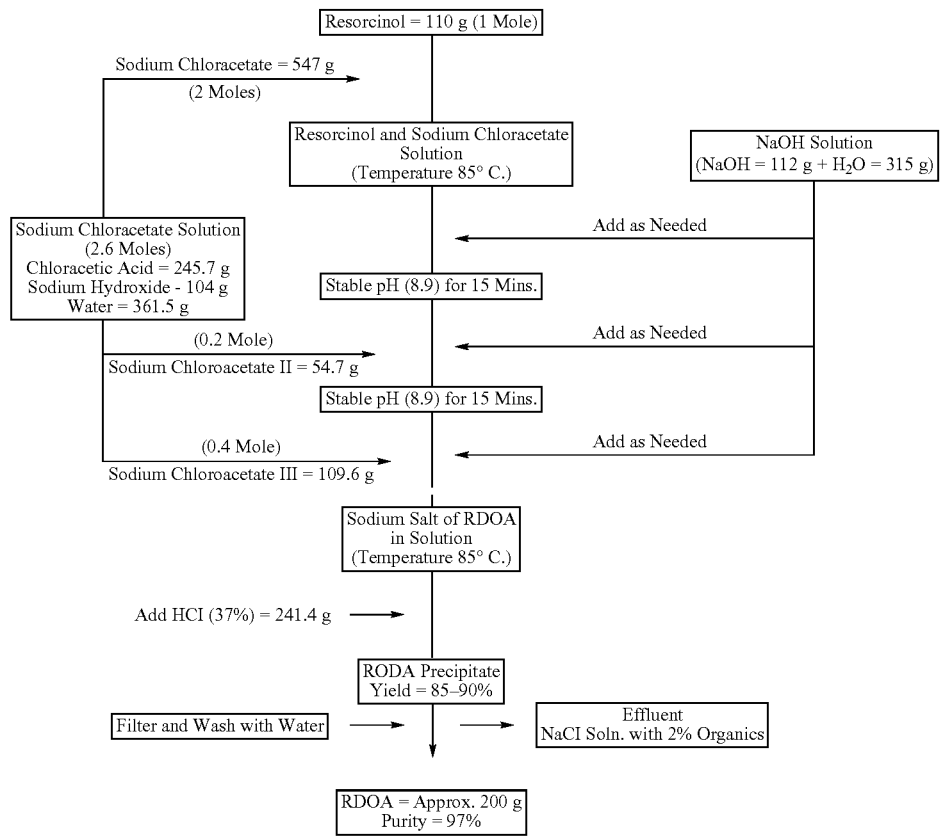

Process Scheme 2

Charge 55 grams of resorcinol (0.5 mole) and 247.1 grams of sodium chloroacetate solution (prepared from 94.5 grams of chloroacetic acid (1 mole), 40 grams of sodium hydroxide and 112.5 grams of water) into a reaction kettle equipped with a stirrer, thermometer, condenser, pH probe and an addition funnel. The solution was stirred under nitrogen atmosphere and heated to about 85 to 95° C. Then the first portion of the sodium hydroxide solution (prepared from 48 grams of sodium hydroxide dissolved in 135 grams of water) was added dropwise in such a way that the pH of the reaction mixture was maintained at 8.2 (or a pre-determined value). When the pH of the reaction solution was stable for 15 minutes at 8.2, the second charge of sodium chloroacetate solution (0.1 mole, 24.7 grams) was added into the reaction mixture. Then, the second portion of sodium hydroxide solution (already taken in the addition funnel) was added dropwise at pH at about 8.2. After determining the pH steady at 8.2 for 15 minutes, a third addition of sodium chloroacetate solution (0.1 mole, 24.7 grams) was carried out. The remaining sodium hydroxide solution left in the addition funnel was added dropwise at 85 to 95° C. During the course of sodium hydroxide additions, the temperature and the pH of the reaction mixture were kept constant and maintained.

The temperature of the reaction mixture was reduced to about 85° C., and then the hydrochloric acid solution (1.2 mole) was added dropwise to liberate resorcinol di(oxyacetic) acid from its sodium salt. The final pH of the reaction mixture after the acidification was between 0.5 to 1.0. After acidifying the reaction mixture, it was cooled to room temperature. The crystals separated were filtered, washed with cold water and dried first under ambient conditions, and then under vacuum.

The yield was 89.7 grams (79.4% of theoretical). The melting point was determined to be 191 to 193° C. NMR analysis of the product showed 98% purity before any further purification.

EXAMPLES 12 THROUGH 15

Example 11 was repeated several times by maintaining the same molar ratios of resorcinol and sodium chloroacetate (at 1:2.6 mole) and temperature. The pH of the reaction mixture was varied (between 8.2 to 10) and maintained constant during the course of sodium hydroxide additions. The experimental details are presented in Table 3.

TABLE 3

Synthesis of Resorcinol Di(Oxyacetic) Acid (RDOA) Using Sodium Chloroacetate
(30% Molar Excess Sodium Chloroacetate; Effect of pH on RDOA Yield; Process Scheme 2)

| | Example | | | | | | | | | |
|---|---|---|---|---|---|---|---|---|---|---|
| | 11 | | 12 | | 13 | | 14 | | 15 | |
| | Moles | Grams | Moles | Grams | Moles | Grams | Moles | Grams | Moles | Grams |
| Raw Materials | | | | | | | | | | |
| Resorcinol | 0.5 | 55 | 0.5 | 55 | 0.5 | 55 | 0.5 | 55 | 0.27 | 30 |
| Sodium Chloroacetate | 1.3 | | 1.3 | | 1.3 | | 1.3 | | 0.7 | |
| Sodium Hydroxide Solution | 1.3 | | 1.3 | | 1.3 | | 1.3 | | 0.7 | |
| Hydrochloric Acid (37% Aqu) | 1.4 | | 1.4 | | 1.4 | | 1.4 | | 1.3 | |
| Reacation Conditions | | | | | | | | | | |
| Temperature (° C.) | 95 | | 95 | | 85 | | 85 | | 90-95 | |
| pH of Reaction Mixture | 8.2 | | 8.5 | | 8.6 | | 8.9 | | 10 | |
| Molar Excess of Chloroacetate (%) | 30 | | 30 | | 30 | | 30 | | 30 | |
| Chloroacetate Addition Steps (#) | 3 | | 3 | | 3 | | 3 | | 3 | |
| Acid (HCl) Addition Temp. (° C.) | 90-95 | | 90-95 | | 85 | | 85 | | 85 | |
| Product Yield (RDOA) | | | | | | | | | | |
| Expected Yield (Theoretical, g) | 113 | | 113 | | 113 | | 113 | | 61.6 | |
| Actual Yield (g) | 89.7 | | 99.4 | | 103.2 | | 101.6 | | 26 | |
| Actual Yield (%) | 79.4 | | 88 | | 91.3 | | 90 | | 42 | |
| Melting Point (° C.) | 191-193 | | 191-193 | | 191-193 | | 191-193 | | 187-190 | |
| NMR Analysis of Product (Wt. %) | | | | | | | | | | |
| RDOA | 98.1 | | 97.2 | | 97.4 | | 97.5 | | 90 | |
| RMOA | 1.4 | | 1.3 | | 1.2 | | 1.2 | | 5.5 | |
| HCPA | 0.5 | | 1.5 | | 1.4 | | 1.3 | | 4 | |

As can be seen from the results of Table 3, the yields of resorcinol di(oxyacetic) acid were higher when the reaction pH was maintained at between 8.6 to 8.9, while pH from about 8.2 to 8.5 also gave good yields.

As demonstrated above, embodiments of the invention provide a method of making phenylene dioxydiacetic acid in relatively high yields. In some embodiments, the yields exceed about 80% or even about 90%. Moreover, the purity of the acid is not obtained at the expense of the yield or products costs. Therefore, the acid can be used in the synthesis of polyester and polyamide.

While the invention has been described with respect to a limited number of embodiments, the specific features of one embodiment should not be attributed to other embodiments of the invention. No single embodiment is representative of all aspects of the invention. In some embodiments, the compositions or methods may include numerous compounds or steps not mentioned herein. In other embodiments, the compositions or methods do not include, or are substantially free of, any compounds or steps not enumerated herein.

Variations and modifications from the described embodiments exist. The method of making the resins is described as comprising a number of acts or steps. These steps or acts may be practiced in any sequence or order unless otherwise indicated. Finally, any number disclosed herein should be construed to mean approximate, regardless of whether the word "about" or "approximately" is used in describing the number. The appended claims intend to cover all those modifications and variations as falling within the scope of the invention.

What is claimed is:

1. A method of making phenylene dioxydiacetic acid, comprising:

contacting a dihydroxybenzene represented by formula (1) under reaction conditions with a salt of haloacetic acid in a solution without adding an external haloacetic acid to produce a salt of phenylene dioxydiacetic acid, wherein the pH of the reaction conditions is from about 7 to about 11; and

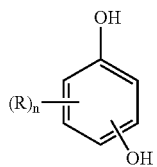

(1)

converting the salt of phenylene dioxydiacetic acid to free phenylene dioxydiacetic acid represented by formula (2):

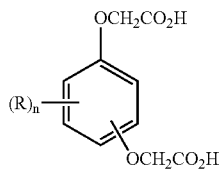

(2)

wherein R represents a hydroxyl, halogen, carboxyl group or hydrocarbon group, and n represents an integer from 0 to 3.

2. The method of claim 1, wherein no dihydroxybenzene salt is used as a starting material.

3. The method of claim 1, wherein the salt of haloacetic acid is formed by reacting a hydroxide with a halo acetic acid before contacting the dihydroxybenzene.

4. The method of claim 1, wherein the reaction mixture obtained in the contacting step has a pH value in the range from about 7 to about 11.

5. The method of claim 1, wherein the reaction mixture obtained in the contacting step has a pH value in the range from about 8 to about 10.

6. The method of claim 1, wherein the reaction mixture obtained in the contacting step has a pH value in the range from about 8.5 to about 8.9.

7. The method of claim 1, wherein the reaction mixture obtained in the contacting step is kept at a temperature in the range of about 70° C. to about 105° C.

8. The method of claim 1, wherein the reaction mixture obtained in the contacting step is kept at a temperature in the range of about 80° C. to about 95° C.

9. The method of claim 1, wherein the reaction mixture obtained in the contacting step is kept at a temperature about 85° C.

10. The method of claim 1, wherein a stoichiometric amount of the salt of a haloacetic acid is contacted with the dihydroxybenzene.

11. The method of claim 1, wherein a molar excess amount of the salt of a haloacetic acid is contacted with the dihydroxybenzene.

12. The method of claim 11, wherein the salt of a haloacetic acid is added to the reaction mixture stepwise.

13. The method of claim 11, wherein the molar excess amount is about 20% to about 30%.

14. The method of claim 4, wherein the pH of the reaction mixture is adjusted by adding an appropriate amount of an alkaline solution.

15. The method of claim 1, wherein the conversion of the salt of phenylene dioxydiacetic acid to free phenylene dioxydiacetic acid is effected by contacting the salt with an acid.

16. The method of claim 15, wherein the acid is hydrochloric acid, sulfuric acid or mineral acid.

17. The method of claim 1, the salt of haloacetic acid is sodium monochloroacetate or sodium monobromoacetate.

18. The method of claim 1, wherein the dihydroxybenzene is resorcinol and the salt of a haloacetic acid is sodium chloroacetate.

19. The method of claim 18, wherein the reaction mixture obtained in the contacting step has a pH value in the range from about 7 to about 11.

20. The method of claim 18, wherein the reaction mixture obtained in the contacting step has a pH value in the range from about 8 to about 10.

21. The method of claim 18, wherein the reaction mixture obtained in the contacting step has a pH value in the range from about 8.5 to about 8.9.

22. The method of claim 18, wherein the reaction mixture obtained in the contacting step is kept at a temperature in the range of about 70° C. to 105° C.

23. The method of claim 18, wherein the reaction mixture obtained in the contacting step is kept at a temperature in the range of about 80° C. to 95° C.

24. The method of claim 18, wherein the reaction mixture obtained in the contacting step is kept at a temperature about 85° C.

25. The method of claim 1, wherein the dihydroxybenzene is resorcinol, hydroquinone, or catechol.

26. A method of making 1,3-phenylene dioxydiacetic acid, comprising:

contacting resorcinol with sodium chloroacetate in an aqueous solution without adding an external chloroacetic acid, wherein the temperature is from about 70° C. to about 95° C. and the pH is from about 8.5 to 8.9 to produce sodium 1,3-phenylene dioxydiacetate.

27. The method of claim 26, wherein the sodium chloroacetate is prepared by reacting a stoichiometric amount of sodium hydroxide with chloroacetic acid before contacting with the resorcinol.

28. The method of claim 26, wherein a stoichiometric amount of sodium chloroacetate is contacted with resorcinol.

29. The method of claim 26, wherein a molar excess amount of sodium chloroacetate is contacted with resorcinol.

30. The method of claim 29, wherein the molar excess amount is about 20% to 30%.

31. The method of claim 26, wherein sodium chloroacetate is added stepwise.

32. The method of claim 26, wherein an aqueous sodium hydroxide solution is used to maintain the pH.

33. The method of claim 26, further comprising converting the sodium 1,3-phenylene dioxydiacetate into free 1,3-phenylene dioxydiacetic acid.

34. A method of making copolymerized polyester resin, comprising:

subjecting a dicarboxylic acid component containing terephthalic acid or its ester derivative as the main component and a phenylene dioxydiacetic acid as a copolymerizable component, and a diol component containing ethylene glycol as the main component, to polycondensation through an esterification reaction or a transesterification reaction, wherein the phenylene dioxydiacetic acid is prepared by:

a) contacting a dihydroxybenzene represented by formula (1) with a salt of haloacetic acid in a solution without adding an external haloacetic acid to produce a salt of phenylene dioxydiacetic acid, wherein the pH of the reaction conditions is from about 7 to about 11; and

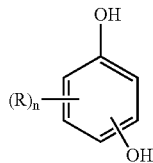
(1)

(b) converting the salt of phenylene dioxydiacetic acid to free phenylene dioxydiacetic acid represented by formula (2):

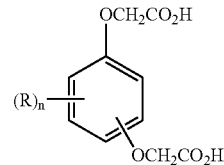
(2)

wherein R represents a hydroxyl, halogen, carboxyl group or hydrocarbon group, and n represents an integer from 0 to 3.

35. The method of claim 34, wherein a batch process is used.

36. The method of claim 34, wherein a continuous process is used.

37. The method of claim 1, wherein the yield of phenylene dioxydiacetic acid is at least about 70%.

38. The method of claim 26, wherein the yield of phenylene dioxydiacetic acid is at least about 70%.

* * * * *